United States Patent [19]

Bloom

[11] 4,152,332

[45] May 1, 1979

[54] METAL COMPLEXES OF CERTAIN HETERO-ETHENE DITHIOLS

[75] Inventor: Stanley M. Bloom, Waban, Mass.

[73] Assignee: Polaroid Corporation, Cambridge, Mass.

[21] Appl. No.: 844,535

[22] Filed: Oct. 25, 1977

Related U.S. Application Data

[62] Division of Ser. No. 536,419, Dec. 26, 1974, Pat. No. 4,062,867, which is a division of Ser. No. 251,284, May 8, 1972, Pat. No. 3,875,199, which is a division of Ser. No. 60,982, Jul. 6, 1970, Pat. No. 3,687,862, which is a division of Ser. No. 577,576, Sep. 2, 1966, Pat. No. 3,588,216.

[51] Int. Cl.$^2$ .................. C07D 207/32; C07D 307/36; C07D 307/79
[52] U.S. Cl. ............................. 260/326.9; 260/346.22; 260/347.2
[58] Field of Search ........... 260/346.22, 326.9, 346.11, 260/347.2

[56] References Cited

U.S. PATENT DOCUMENTS

| | | | |
|---|---|---|---|
| 3,705,919 | 12/1972 | Heck | 260/346.22 |
| 3,806,462 | 4/1974 | Bloom | 260/326.9 |

*Primary Examiner*—Alton D. Rollins
*Attorney, Agent, or Firm*—Gaetano D. Maccarone; John P. Morley

[57] ABSTRACT

A metal complex of the formula:

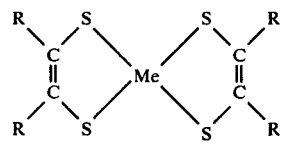

wherein Me is nickel, platinum or palladium and each R is the same radical selected from the group consisting of:

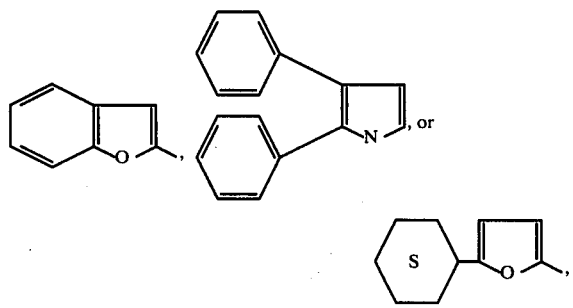

useful for imparting IR absorbing characteristics to plastics.

4 Claims, 6 Drawing Figures

METAL COMPLEXES OF CERTAIN HETERO-ETHENE DITHIOLS

CROSS REFERENCE TO RELATED APPLICATIONS

This application is a division of U.S. Patent Application Ser. No. 536,419 filed Dec. 26, 1974 now U.S. Pat. No. 4,062,867 which is a division of U.S. Patent Application Ser. No. 251,284 filed May 8, 1972 and now U.S. Pat. No. 3,875,199 which is a division of U.S. Patent Application Ser. No. 60,982 filed July 6, 1970 and now U.S. Pat. No. 3,687,862 which in turn is a division of Application Ser. No. 577,576 filed Sept. 2, 1966 and now U.S. Pat. No. 3,588,216.

This invention relates to infrared (IR) absorption and, more particularly to novel products and procedures directed thereto.

A primary object of this invention, therefore, is to provide novel plastic products including means for absorbing in the infrared, particularly in the near infrared, and novel processes employing the same.

Another object is to provide novel products and processes for diminishing to an appropriate extent transmission of light both in the visible and in the infrared regions of the spectrum.

A further object is to provide novel plastic optical elements including an infrared absorber.

Still another object is to provide novel light-polarizing elements including means for absorption in the infrared.

Yet another object is to provide a novel sunglass structure having a plastic optical system including light-polarizing means and means for absorption in the infrared.

A still further object is to provide a class of compounds particularly useful for precluding transmission of infrared and novel processes employing the same.

Other objects of the invention will in part be obvious and will in part appear hereinafter.

The invention accordingly comprises the processes involving several steps and the relation and order of one or more of such steps with respect to each of the others, and the products possessing the features, properties and the relation of elements which are exemplified in the following detailed disclosure, and the scope of the application of which will be indicated in the claims.

For a fuller understanding of the nature and objects of the invention, reference should be had to the following detailed description taken in connection with the accompanying drawing wherein.

Figure 1:
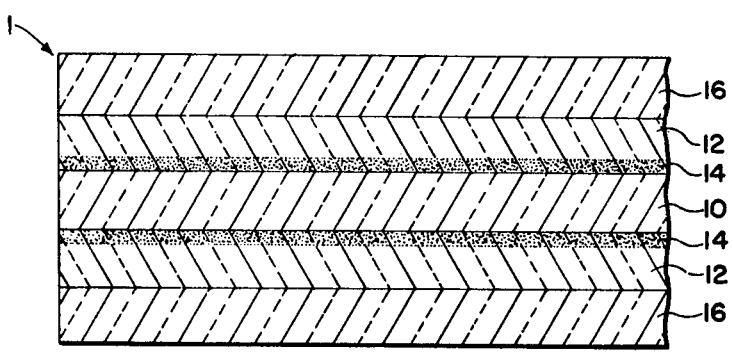
FIG. 1 is an enlarged diagrammatic sectional view of a novel lens system for sunglasses or the like according to this invention.

As was mentioned previously, one aspect of the present invention is directed to compounds which are especially useful for inhibiting transmission of infrared radiation, particularly in the near infrared, i.e., absorbing infrared radiation, and to products and processes employing these compounds.

The infrared absorbers contemplated for use in the present invention may be defined as a metal complex of a bis-[cis-1,2-bis-(alkyl, hydrogen, aryl or heterocyclic-)ethylene-1,2-dithiolate]. They may also be defined more simply as ene dithiol metal complexes.

These infrared absorbers may be represented by the following formula:

$$\begin{array}{c} R \diagdown \phantom{C} S \diagdown \phantom{M} S \diagup \phantom{C} R \\ \phantom{R} C \phantom{\diagdown S \diagdown M S \diagup} C \\ \phantom{R} \| \phantom{C \diagdown S \diagdown} Me \phantom{S \diagup C} \| \\ \phantom{R} C \phantom{\diagdown S \diagdown M S \diagup} C \\ R \diagup \phantom{C} S \diagup \phantom{M} S \diagdown \phantom{C} R \end{array} \quad (A)$$

wherein:

Me is a metal of the first, second or third transition metal series, i.e. those elements of Group VIII of the table of periodic arrangement of the elements, e.g. nickel, palladium, or platinum, which will provide a complex which is an effective IR absorber and which is substantially or effectively transparent to light in the visible region of the spectrum, e.g. from about 400–700 m$\mu$;

each R, which may be the same or different, is hydrogen, alkyl, an aromatic or heterocyclic ring, or a substituted derivative thereof, e.g. alkoxyalkyl, alkyl and/or alkoxy-substituted aromatic and heterocyclic rings, substituents of the foregoing description containing electron withdrawing groups, etc.

As examples of useful alkyl radicals contemplated by said R moieties, mention may be made of lower alkyl radicals containing 1–6 carbon atoms, e.g. methyl, ethyl, propyl, isopropyl, butyl, etc. As examples of useful aromatic rings, including substituted derivatives thereof, mention may be made of phenyl, naphthyl, methyl-phenyl, methylnaphthyl, alkoxyphenyl and alkoxynaphthyl, e.g. dodecyloxyphenyl, halo-substituted, particularly fluoro-substituted, -S-alkyl-substituted, amino, including dialkylamino-substituted, haloalkyl-substituted, e.g. trifluoromethyl-substituted phenyl and naphthyl radicals, etc.

As examples of useful heterocyclic rings, mention may be made of those of the formula:

$$\underset{X}{\boxed{\phantom{XXX}}}$$

where X is nitrogen, oxygen, or sulfur, and substituted derivatives thereof, including benz-substituted derivatives.

The following compounds are illustrative of useful IR absorbers within the scope of Formula (A):

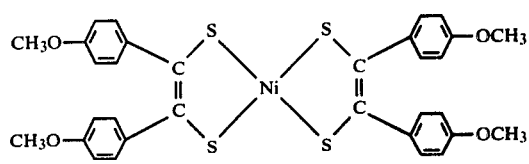
(2)
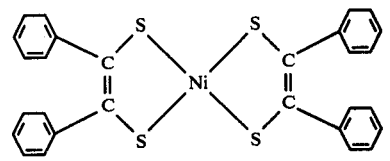
(3)
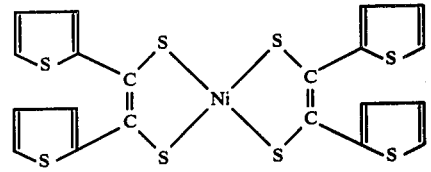
(4)
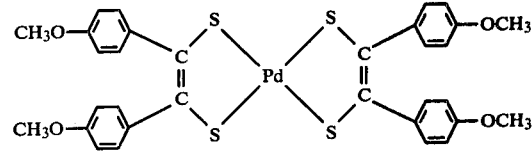
(5)
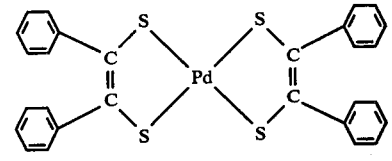
(6)
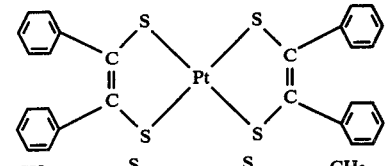
(7)
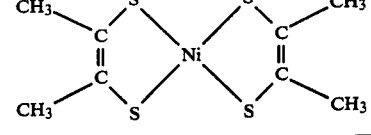
(8)
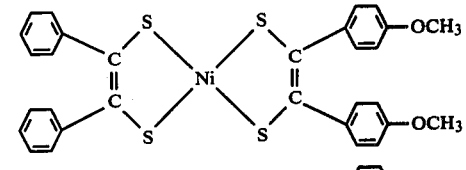
(9)
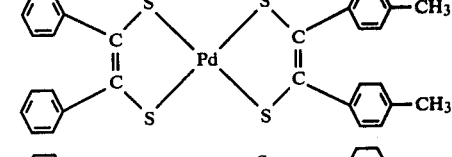
(10)
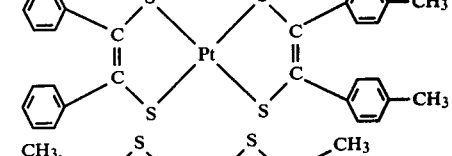
(11)

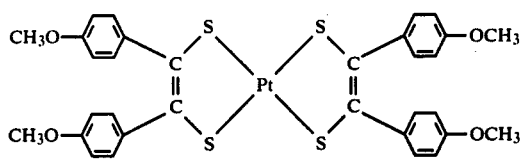 (12)

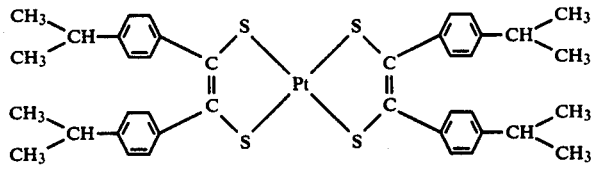 (13)

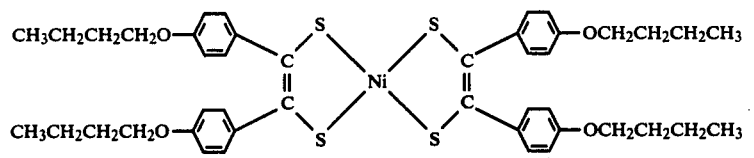 (14)

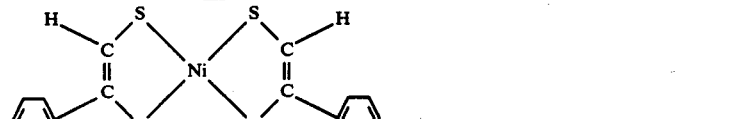 (15)

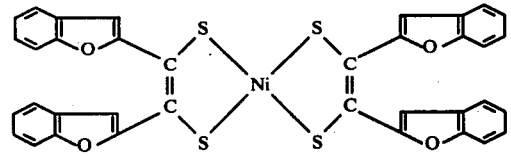 (16)

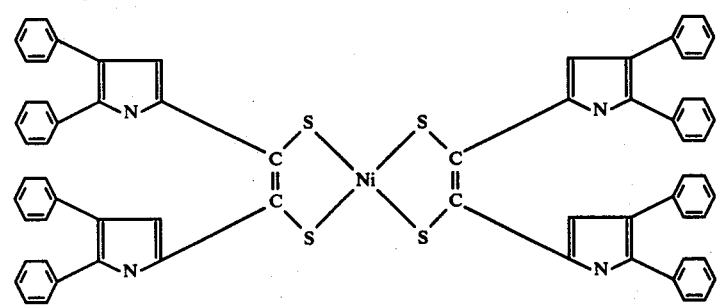 (17)

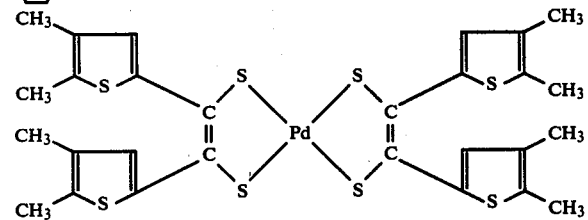 (18)

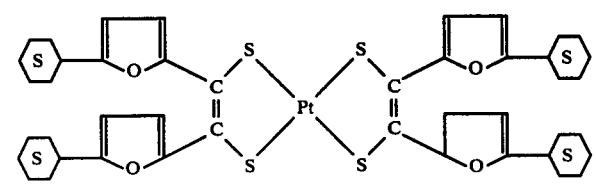 (19)

The compounds of Formula A are in general previously known in the art, although certain of the disclosed species, particularly the asymmetrical species, e.g., those of Formulae 3, 8, 9, 10, 13, 14, 16, 17, 18, and 19 are believed to be specifically novel. (See for example, the article by Schrauzer and Mayweg, "Preparation, Reactions, and Structure of Bisdithio-α-diketone Complexes of Nickel, Palladium, and Platinum". J.A.C.S., 87:7, pp 1483–1489.) The compounds of Formula A may accordingly in general be prepared in the manner heretofore described in the literature.

For example, they may be prepared by reacting P$_4$S$_{10}$ with a compound of the formula:

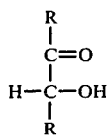
(B)

wherein R has the meaning heretofore noted, to form a compound of the formula:

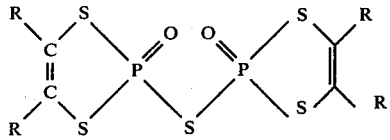
(C)

which is then reacted with a suitable inorganic salt containing the desired metal, Me, e.g., $NiCl_2 \cdot 6H_2O$, $PtCl_2$, $PdCl_2$, $K_2PtCl_4$, $K_2PdCl_4$, etc. to prepare the desired compound of Formula A. Symmetrical compounds, i.e. where each R is the same, are obtained by using a single compound of Formula B wherein each R is the same. Asymmetrical compounds (such as those of Formulae 8 and 9) may be obtained by employing two different compounds of Formula B as starting materials. In like manner, one or two compounds of Formula B in which each R is different, may be employed to provide compounds of Formula A wherein two or more of the R moieties are different.

The compounds of Formula (A) have been found to possess exceptionally desirable spectral absorption characteristics. As a class, they have been found to be relatively "narrow band" absorbers which have a $\lambda_{max}$ in the near infrared region of the spectrum, substantially no absorption in the visible region, i.e. are substantially transparent to visible light, and a $\lambda_{max}$ in the ultraviolet region of the spectrum, primarily in the far ultraviolet region. They are thus particularly useful in optical systems wherein it is desired to transmit visible light while absorbing light in the designated invisible regions of the spectrum, that is, to reduce or minimize transmission in the near infrared and/or in the ultraviolet region of the spectrum. The spectral absorption characteristics of these compounds may be more readily understood by reference to FIGS. 5 and 6 wherein spectral absorption curves of two compounds illustrative of the class, specifically, those of Formulae 5 (shown in dotted line) and 6 (shown in solid line) are superposed. It will be observed that the $\lambda_{max\ IR}$ and $\lambda_{max\ UV}$ of the compounds are shifted by substitution of the complexing metal. They may also be shifted by substitution of the complexing metal. They may also be shifted by changing the substituents of the R moiety, so that by so doing it is possible to provide narrow band filters for various portions of the IR and UV regions of the spectrum.

In addition to their exceptional spectral absorption characteristics, the compounds have been found to be extremely stable to the degradative forces of light, heat, and humidity. Since IR absorbers as a class are quite unstable to such conditions, this stability of those compounds of Formula A is quite surprising.

A representative class of these compounds was tested for stability to light, heat, and humidity by imbibing onto each of three sheets of cellulose acetate butyrate a solution consisting of the compound to be tested dissolved in a suitable organic solvent. Each of the imbibed sheets was then subjected to one of the following standard test procedures: (1) light stability under a xenon arc lamp; (2) relative humidity (moisture plus heat); and (3) dry heat. Stability was tested by determining the density before and after each test. The following chart shows the results of these tests, the figures given representing the percent of fading (loss of density) after the recited time interval.

TABLE I

| Compound (Formula No.) | Solvent | Xenon Arc (U.V. Shield) | Relative Humidity (95% at 150° F.) | Dry Heat (150° F.) |
|---|---|---|---|---|
| 1 | tetrahydrofuran | 2.4% (120 hrs) | 0.0% (250 hrs) | 8.2% (250 hrs) |
| 2 | CHCl$_3$ | 0.0% (120 hrs) | 2.0% (120 hrs) | 0.0% (120 hrs) |
| 4 | CHCl$_3$ | 2% (170 hrs) | 3% (170 hrs) | 5% (170 hrs) |
| 7 | tetrahydrofuran | 3.5% (120 hrs) | 2.3% (250 hrs) | 3.5% (250 hrs) |
| 8 | CHCl$_3$ | 2.6% (175 hrs) | 1.7% (175 hrs) | 1.3% (175 hrs) |
| 12 | CHCl$_3$ | 3.0% (170 hrs) | 3.4% (170 hrs) | 0.0% (170 hrs) |

As was mentioned previously, the aforementioned infrared absorbers are particularly useful in plastic optical products which, unlike glass optical products, do not possess a molecular structure that will inherently absorb in the infrared region. Of particular interest in the practice of this invention are plastic sunglasses such as those known in the art as polarizing sunglasses.

A typical plastic sunglass of this nature has an optical system comprising a light polarizer laminated between two sheets of transparent plastic, the outer or free surfaces of which may be provided with an abrasive-resistant coating. The polarizing sheet may for example be a molecularly oriented plastic sheet material which has been stained or dyed to render it light polarizing, e.g. molecularly oriented polyvinyl alcohol stained with iodine; the transparent plastic between which the polarizing sheet is laminated may, for example, be a thermoplastic cellulose derivative, e.g. cellulose nitrate, cellulose triacetate, cellulose acetate propionate, cellulose acetate butyrate, ethyl cellulose, etc.; and the abrasive-resistant coating may, for example, be a completely polymerized melamineformaldehyde resin, a thermosetting, cross-linked polymer such as a diethylenic-substituted polyalkyleneglycol, e.g. polymeric coatings formed by in situ polymerization of polyalkyleneglycol diesters of α-β-unsaturated carboxylic acids on the plastic sheet material, etc. Plastic laminations including materials of this description are disclosed for example, in U.S. Pat. Nos. 2,237,567; 2,527,400; 2,554,850; 3,081,192; and 3,097,106.

While polarizing sunglasses of the foregoing description effectively diminish transmission of visible light to a desired comfortable level, e.g. to say from about 20–30% of the visible solar energy, an appreciable amount of invisible radiation, primarily in the ultraviolet and near infrared regions of the spectrum, is transmitted. By way of illustration, the solar energy at the lens of the eye is shown by one of the superposed curves on FIG. 4. From this curve it will be seen that appreciable solar energy both in the near infrared and in the ultraviolet regions of the spectrum is present at the lens.

The ultraviolet is substantially absorbed at the lens, but the IR passes through.

In view of the foregoing discussion, it is quite surprising that while it has heretofore been suggested to employ ultraviolet absorbers in such optical products to protect the lens, it is believed and understood that no one has heretofore employed an IR absorber in such plastic optical products. The failure to do so is believed to be at least in part due to the inherent instability to light of IR absorbers as a class and may in part be due to the failure to appreciate the advantages of employing such IR absorbers. Infrared absorbers which also have good ultraviolet absorption, as herein disclosed, thus minimize transmission of radiation which may be harmful to the eye.

An important aspect of this invention, therefore, is the concept of employing an infrared absorber in plastic optical products such as sunglasses of the foregoing general description.

Figure 2:
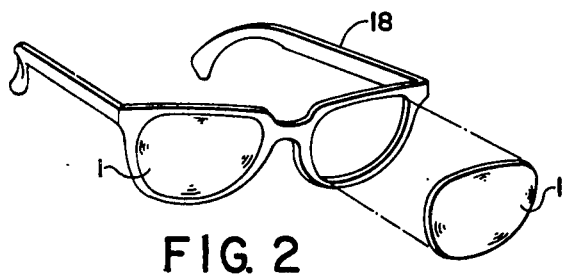
FIG. 2 is a partially exploded, perspective view of novel sunglasses or the like having the lens system of FIG. 1.
Figure 3:
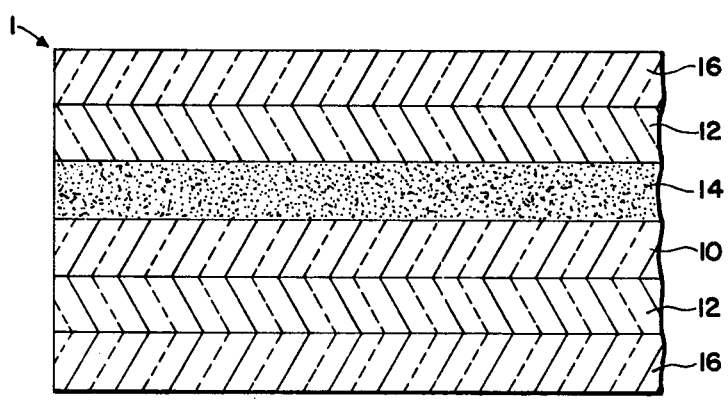
FIG. 3 is a view similar to FIG. 1 of another lens system of this invention.

This aspect of the invention will be more readily understood by reference to FIGS. 1-3 of the accompanying drawings.

As shown in FIG. 1, one embodiment of this aspect of the invention comprises a plastic optical element 1, the outer surfaces of which are provided with an abrasive-resistant coating 16, such as those heretofore described. Between these outer layers are positioned, as by lamination, a pair of substantially or effectively transparent sheets of plastic 12, e.g. cellulose acetate butyrate, cellulose nitrate, cellulose acetate propionate, cellulose acetate, ethyl cellulose, etc; a pair of layers or coatings 14 containing an IR absorber, e.g. one or more of the IR absorbers of Formula A, and a polarizing sheet material 10, e.g. a molecularly oriented polyvinyl alcohol sheet which has been stained with iodine to render it light-polarizing and which may also have been borated in the manner disclosed in any of U.S. Pat. No. 2,445,579, U.S. Pat. No. Re: 23,297 or U.S. Pat. No. 2,554,850.

The thickness of the various layers in the aforementioned plastic optical elements are not critical and may vary over wide ranges. It will be appreciated, however, that the layers are preferably as thin as possible, for reasons of economy, weight and to minimize distortion or refraction of transmitted light. By way of example only, the abrasion-resistant coating layers each may be on the order of 1 mil thick; the transparent plastic sheets may each be on the order of 0.0120-0.0140" thick; the polarizer on the order of 0.001" thick; and the IR absorber-containing layers each on the order of about 0.1 to about 5.0 mils thick.

The IR absorber-containing layers may be applied as a coating comprising a viscous solution containing the same or they may be imbibed into the transparent plastic sheets by contacting them with a solution containing one or more of the absorbers. The former method of application is preferred, however, since it has been found that greater amounts of the absorber can be added as a coating than can be added by imbibition. It will be appreciated, however, that even when applied as a coating, some of the absorber may inherently be imbibed. Whether the IR absorber is added as a coating or by imbibition, useful solvents for that purpose include chloroform, methylene dichloride, toluene, tetrahydrofuran, etc., and mixtures of such solvents.

In addition to the layers or coatings shown in FIG. 1, the element may contain other layers introduced to provide suitable bonding surfaces to insure obtaining a strong lamination.

It will be appreciated that the plastic element is not restricted to the relationship of layers shown in FIG. 1. For example, the IR absorber may be present between the outer coating 16 and the transparent plastic sheet 12. (In the event a scratch resistant coating 16 is applied by in situ polymerization, care should be exercised to avoid the use of polymerization catalysts, e.g., peroxides, which might attack the infrared absorber.) In lieu of having two separate layers 14 of IR absorber, a single such layer may be provided, as shown in FIG. 3. In any event, optical elements of this invention may be employed in conventional eyeglass frames 18, as shown in FIG. 2.

Figure 5:
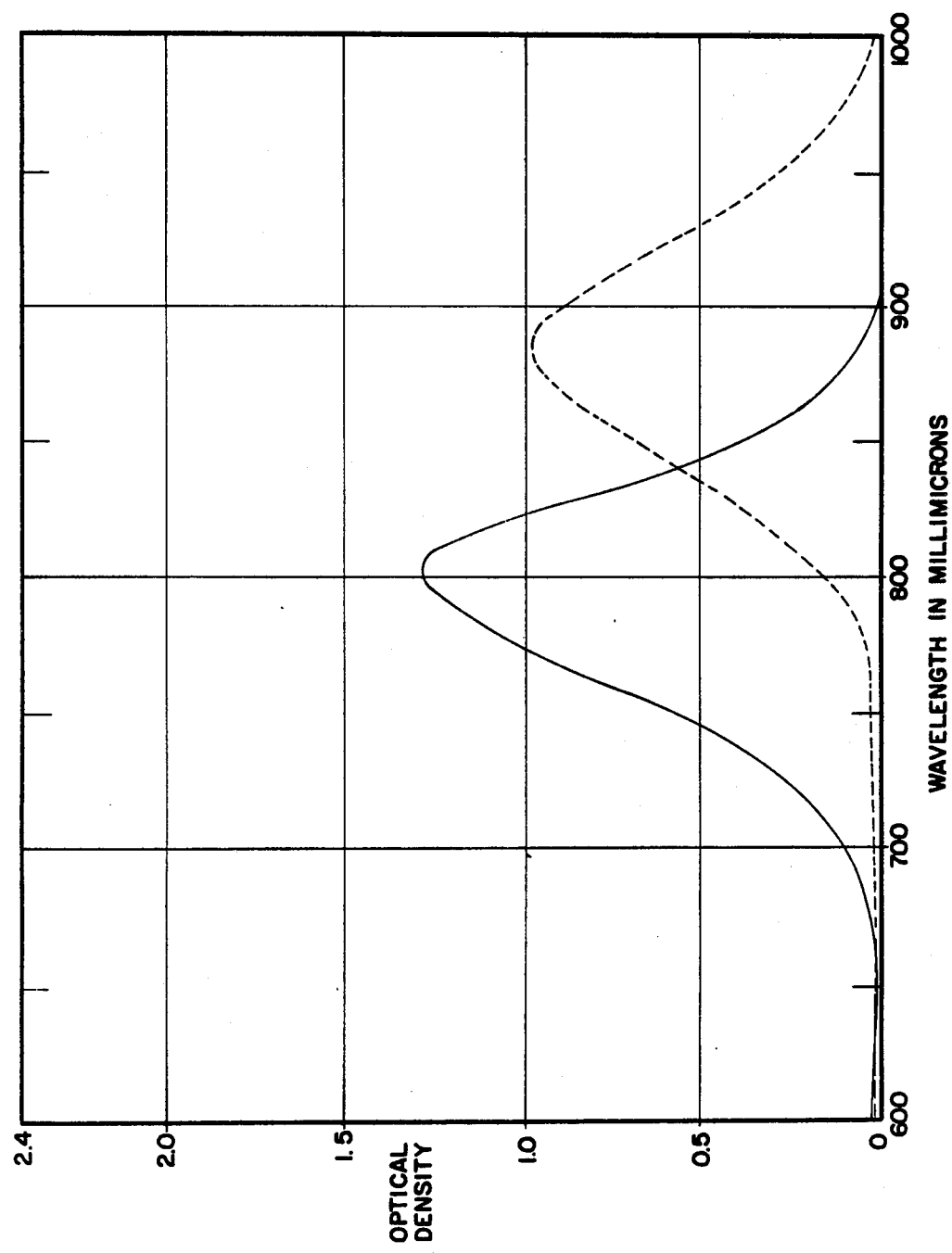
FIGS. 5 and 6 are graphic presentations of the light transmittance curves of the IR absorbers illustrative of the class of absorbers contemplated by this invention.
Figure 6:
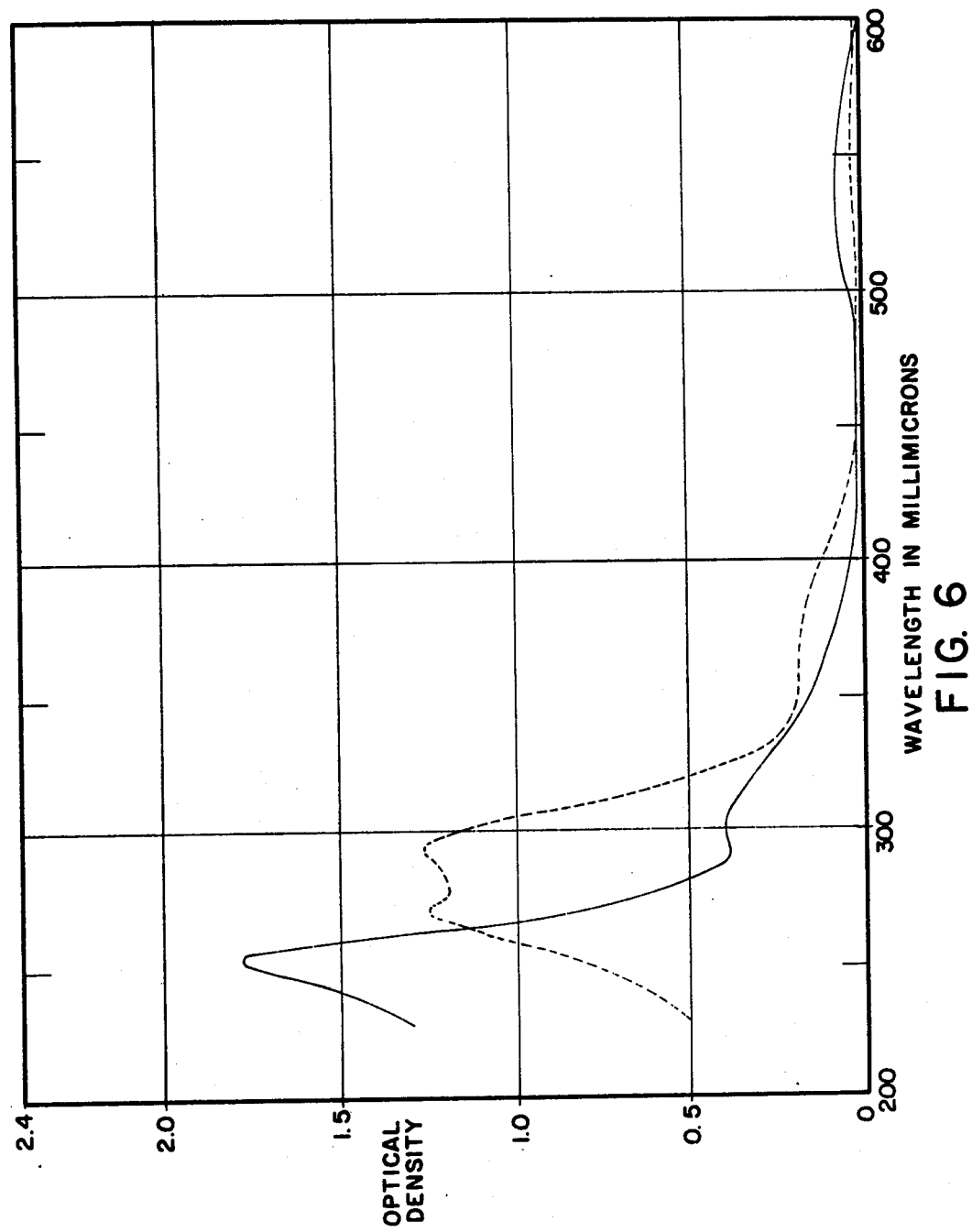

As was mentioned earlier and illustrated in the spectral absorption curves shown in FIGS. 5-6, while the compounds of Formula A are extremely good absorbers in the near infrared region of the spectrum and are substantially transparent to visible light, they also absorb appreciably in the ultraviolet region. This latter property makes it possible to eliminate or to materially reduce the amount of ultraviolet absorber needed in such an element to protect the lens of the eye. Thus, these compounds may be said to serve a dual function in reducing the transmission of harmful invisible radiation at both ends of the spectrum.

The amount of the IR absorber employed in the plastic optical elements of this invention may vary over a wide range, the amount employed being in part dependent upon the percent of transmission in this region desired and is in part dependent upon the efficiency of the absorber in the system employed. In a preferred embodiment, however, the IR absorber is present in an amount such that the amount of transmitted IR is not substantially greater, if greater at all, than the amount of visible light transmitted. By not "substantially greater", it is meant that the percent of IR transmitted does not exceed the percent of visible light transmitted by more than about 5%.

Since the compounds of Formula A are relatively narrow band absorbers, it may be desirable to employ a mixture of two or more such compounds of varying $\lambda_{max}$ to provide effective absorption over the necessary range of the infrared region of the spectrum.

While the foregoing description of plastic optical elements has, for purposes of illustration, been in terms of polarizing sunglasses, it will be appreciated that the invention is not limited thereto. Since an important aspect of this invention is the discovery that compounds of Formula A effectively diminish transmission of substantial amounts of unwanted invisible radiation while being substantially transparent to visible light and possessing extremely desirable stability to light, heat and humidity, this invention also contemplates the use of the compounds of Formula A in various systems wherein it is desired to transmit visible light but to diminish or retard transmission of invisible radiation in particular regions of the spectrum. Since these compounds possess narrow absorption bands they may be employed singly to provide absorption in a particular narrow band of the spectrum or in combination to provide broader absorption. The ability of the individual compounds to provide narrow absorption in a desired region is a significant advantage which will be apparent to those skilled in the art. Accordingly, the various other systems to which this invention is applicable, e.g. in plastic lenses for use in photography, will be readily suggested to those skilled in the art in the light of this description.

The following examples show by way of illustration and not by way of limitation the preparation of the novel compounds of this invention, the $\lambda_{max}$ of each of the compounds being determined in dichloromethane.

EXAMPLE 1

The IR absorber of Formula I was prepared by refluxing 1 mole of:

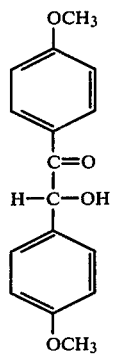

with 1.25 mole of $P_4S_{10}$ in dioxane (inert solvent) for four hours. The mixture was then cooled and filtered, after which was added 1 mole of $NiCl_2\cdot 6H_2O$ dissolved in water. The resulting mixture was then heated on a steam bath for two hours to form the compound of Formula 1 which was collected by cooling and filtering to yield a crystalline product, m.p. 292° C., $\lambda_{max}=920$ m$\mu$; $\epsilon=35,000$.

EXAMPLE 2

Substitution of benzoin for the acyloin of Example 1 yielded the compound of Formula 2, m.p. 282°–283° C. $\lambda_{max}=865$ m$\mu$; $\epsilon=29,600$.

EXAMPLE 3

Substitution of:

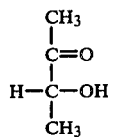

in the procedure of Example 1 yielded the compound of Formula 7, m.p. 255°–256° C.; $\lambda_{max}=773$ m$\mu$; $\epsilon=19,600$.

EXAMPLE 4

Repetition of Example 1, employing a large excess of benzoin to avoid loss of the metal, and employing $K_2PtCl_4$ yielded the compound of Formula 6, m.p. 310° C.; $\lambda_{max}=800$ m$\mu$; $\epsilon=51,600$.

EXAMPLE 5

Substitution of the acyloin in the procedure of Example 4 yielded the compound of Formula 12, m.p. 303°–305° C.; $\lambda_{max}=863$ m$\mu$; 41,600.

EXAMPLE 6

Substitution of:

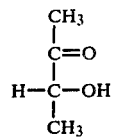

in the procedure of Example 4 yielded the compound of Formula 11, m.p. >350° C.; $\lambda_{max}=740$ m$\mu$; $\epsilon=36,800$.

EXAMPLE 7

Substitution of $K_2PdCl_4$ in the procedure of Example 4 yielded the compound of Formula 5, m.p. 254° C.; $\lambda_{max}=885$ m$\mu$; $\epsilon=39,700$.

EXAMPLE 8

Substitution of $K_2PdCl_4$ in the procedure of Example 5 yielded the compound of Formula 4, m.p. >250° C.; $\lambda_{max}=948$ m$\mu$; $\epsilon=37,900$.

EXAMPLE 9

4,4'-diisopropyl benzoin was prepared according to the synthesis described in Ber., 77, 409 (1944). This compound was substituted for the acyloin in the procedure of Example 1 to yield the compound of Formula 13, m.p. 305°–307° C.; $\lambda_{max}=828$ m$\mu$; $\epsilon=49,200$.

EXAMPLE 10 p-butoxybenzaldehyde was made by the method described in Stoermer, Ber. 61,2328 (1928). This was in turn used to make 4,4'-dibutoxybenzoin in the manner described in Tadros, *J. Chem. Soc.*, (1963), 4527. Substitution of this benzoin for the acyloin of Example 1 yielded the compound of Formula 14, m.p. 239°–240° C.; $\lambda_{max}=930$; $\epsilon=35,600$.

EXAMPLE 11

Substitution of $\alpha$-bromoacetophenone for the acyloin of Example 1 yielded the compound of Formula 15 as an impure mixture which was not purified. HBr gas was evolved during the reaction. Analysis of the impure cpd; $\lambda_{max}=815$ m$\mu$; $\epsilon=7000$.

EXAMPLE 12

The thenoin:

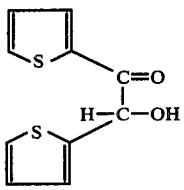

was synthesized according to the procedure described in *J. Org. Chem.* 14, 184 (1949). 20 g. of this compound (0.088 mole) and 57.5 g. of $P_2S_5$ (0.13 mole) were refluxed with stirring for six hours in 300 ml. of dioxane. The reaction mixture was cooled and a black residue was filtered off. To the filtered solution was then added 20.8 g. of $NiCl_2\cdot 6H_2O$ (0.088 mole) dissolved in 100 ml. of $H_2O$. The mixture was heated on a steam bath for one hour to form black crystals which were collected by cooling and filtering to yield 1.1 g. of the compound of Formula 3. This compound was purified by dissolving the crude product in 600 ml. of $CHCl_3$, filtering and evaporating the $CHCl_3$ down to about 25 ml. and allowing the product to crystallize out. m.p. 250°–251° C.; $\lambda_{max}=970$ m$\mu$; $\epsilon=24,600$.

EXAMPLE 13

The procedure of Example 1 was repeated using as starting materials a 3:1 ratio of benzoin to anisoin to yield the compound of Formula 8, m.p. 261°–263° C.; $\lambda_{max}=895$ m$\mu$; $\epsilon=28,400$.

EXAMPLE 14

Substitution of $K_2PtCl_4$ in the procedure of Example 13 yielded the compound of Formula 10, m.p. 288°–290° C., $\lambda_{max}=838$ m$\mu$; $\epsilon=42,000$.

The following example shows by way of illustration and not by way of limitation the preparation of an optical element in accordance with this invention.

EXAMPLE 15

To 100 cc of chloroform was added 7.5 g. of cellulose acetate butyrate chips. To the resulting viscous solution was added a second solution containing 0.1 g. of the IR absorber of Formula 1, 0.1 g. of the IR absorber of Formula 7, and 0.02 g. of "Calco Oil Violet ZIRS" (tradename of American Cyanamid Company for a violet dye which was employed to provide a neutral gray product) in 20 cc. of chloroform. The resulting mixture was coated onto each of two sheets of clear cellulose acetate butyrate at a speed of 6 ft/minute to provide on each sheet a layer containing 0.020 g. of combined IR absorbers per sq. ft. of surface area, the layer or coating being approximately 0.3 mil thick. On the free surface of each sheet of cellulose acetate butyrate (the surface opposite from that containing the IR absorber coating) there was then applied an abrasive-resistant coating such as described in Example 1 of the aforementioned U.S. Pat. No. 3,097,106 containing 0.6% by weight of "Uvinul 490" (tradename of General Aniline Company for an ultraviolet light absorber). The cellulose acetate butyrate on the surface of each of the IR absorber-cellulose acetate butyrate coating was converted back to cellulose by treating it with a 1:1:1 solution of sodium hydroxide, methanol and distilled water for 16 seconds at 46° C. The converted surface of each sheet was then washed and the two sheets were heated in an oven to drive off excess moisture. A solution containing 1.5 g. of polyvinyl alcohol (PVA) in 66.7 cc of water and 33.3 cc of methanol was coated on each of the converted surfaces at 6 ft/minute to provide a suitable bonding surface for the polarizer to be laminated therebetween. A molecularly oriented PVA (stretched four times its original length) was laminated to the PVA coating on one of the sheets at room temperature by applying to the respective laminating surfaces a laminating dope comprising a 2% PVA solution in water and pressing the surfaces together. The molecularly oriented PVA was then stained by imbibition in an iodine solution to render it light-polarizing. It was then imbibed in a boric acid solution of low concentration, dried in vacuo to remove excess liquid, and baked in a heating chamber to dry. The other sheet was then laminated in a similar manner to the free outer surface of the polarizer to provide a plastic optical product containing two of the IR absorbers.

Figure 4:
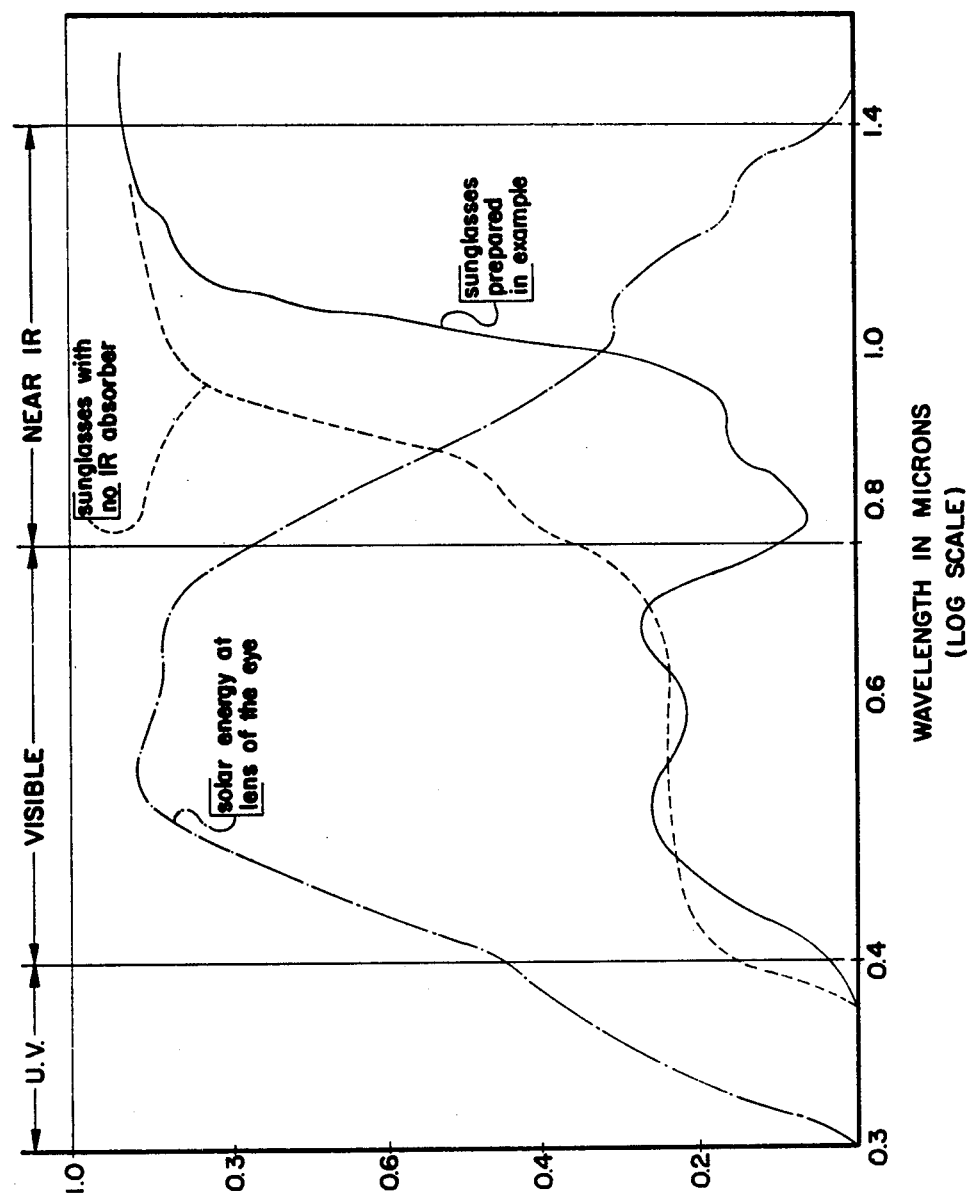
FIG. 4 is a graphic presentation including superposed curves showing the light transmittance of a plastic sunglass lens with and without the IR absorbers of this invention.

The plastic sunglasses prepared in Example 15 were compared with a similar pair prepared in substantially the same manner but containing no IR absorbers. The latter sunglasses also contained a substantially greater amount of ultraviolet absorber than that which was added to the abrasive-resistant coating in the example. For comparison purposes, the respective sunglasses were identical in all other relevant components. The transmission curves of the respective sunglasses are shown in FIG. 4. superposed with the previously mentioned curve showing the solar energy at the lens of the eye.

Looking first at the ultraviolet region (left sides of the graph), it will be noted that the sunglasses without the IR absorber greatly diminish the ultraviolet at the lens, transmitting 4% of the total ultraviolet while the sunglasses with the IR absorber nearly precluded any ultraviolet transmission, transmitting only 0.6% of the total ultraviolet thereby indicating the superiority of the sunglasses of this invention in the ultraviolet region.

With reference next to the visible region of the spectrum, the sunglasses without the IR absorber transmitted 24% of the Kv (energy transmitted at middle visual range, i.e. about 550 m$\mu$); whereas the sunglasses containing the IR absorber transmitted only slightly less, 23%, thus indicating that there is no significant difference in transparency to visible light as a result of the incorporation of the infrared absorbers of this invention.

In the near IR region (right hand side), the sunglasses without the IR absorber transmitted 59.5% of the total near infrared energy otherwise available at the lens of the eye; whereas the sunglasses with the absorber transmitted only 28% of the total radiation in this region. It will thus be seen that the latter sunglasses transmit no substantially greater percent of the IR than they do visible light. It will be appreciated, moreover, that by employing one or more additional IR absorbers having a $\lambda_{max}$ more towards the far infrared, the transmitted near infrared shown on the chart may be further reduced to levels as low or lower than the transmitted visible light.

As was mentioned previously, the asymmetrical compounds of Formula A are specifically novel. These compounds provide the significant advantage of making it possible to provide a particular compound having absorption properties over a particular desired narrow band of the infrared region. By way of illustration, it will be noted from the illustrative examples that the symmetrical compounds of Formulae 1 and 2 have $\lambda_{max}$ respectively of 920 m$\mu$ and 865 m$\mu$. Assuming it is desired to obtain a compound having a $\lambda_{max}$ intermediate these two points in the spectrum, one may prepare the compound of Formula 8, which it will be noted has a $\lambda_{max}$ of 895 m$\mu$.

In Example 15 illustrating the preparation of a plastic optical element in accordance with this invention, reference has been made to the step of converting the cellulose acetate butyrate on the surface of the IR absorber-cellulose acetate butyrate coating back to cellulose. This concept is described and claimed in the copending application of Harold O. Buzzell, Ser. No. 577,578 filed Sept. 2, 1966 and now U.S. Pat. No. 3,620,888.

Since certain changes may be made in the above product and processes without departing from the scope of the invention herein involved, it is intended that all matter contained in the above description or shown in the accompanying drawings shall be interpreted as illustrative and not in a limiting sense.

What is claimed is:
1. A compound of the formula:

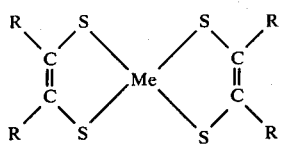
where Me is a metal selected from the group consisting of nickel, platinum or palladium and each R is the same radical selected from the group consisting of
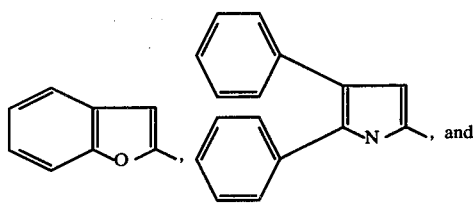, 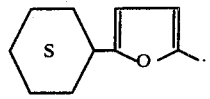
2. A compound of claim 1 of the following formula:
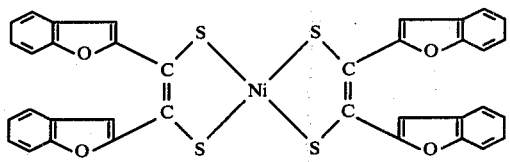
3. A compound of claim 1 of the following formula:
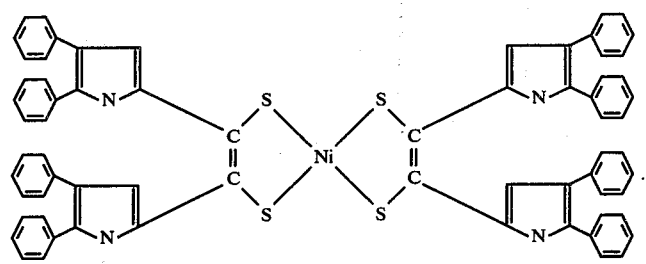
4. A compound of claim 1 of the following formula:
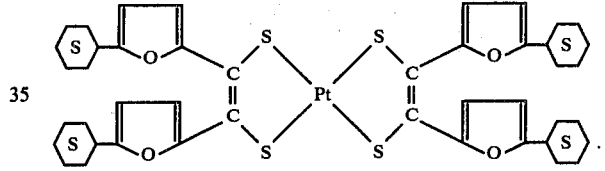
* * * * *